United States Patent
Choudary et al.

(10) Patent No.: US 6,815,566 B2
(45) Date of Patent: Nov. 9, 2004

(54) SUPPORTED OSMATES, PROCESS FOR PREPARATION THEREOF, AND A PROCESS FOR THE PREPARATION OF CHIRAL VICINAL DIOLS USING SUPPORTED OSMATE CATALYST

(75) Inventors: Boyapati Manoranjan Choudary, Andhra Pradesh (IN); Naidu Sreenivasa Chowdari, Andhra Pradesh (IN); Mannepalli Lakshmi Kantam, Andhra Pradesh (IN); Kondapuram Vijaya Raghavan, Andhra Pradesh (IN)

(73) Assignee: Council of Scientific and Industrial Research, New Delhi (IN)

( * ) Notice: Subject to any disclaimer, the term of this patent is extended or adjusted under 35 U.S.C. 154(b) by 0 days.

(21) Appl. No.: 10/460,468

(22) Filed: Jun. 13, 2003

(65) Prior Publication Data

US 2003/0212300 A1 Nov. 13, 2003

Related U.S. Application Data

(60) Division of application No. 10/096,071, filed on Mar. 13, 2002, now Pat. No. 6,646,168, which is a continuation-in-part of application No. 09/983,231, filed on Oct. 23, 2001, now Pat. No. 6,552,234.

(51) Int. Cl.$^7$ .............................................. C07C 33/26
(52) U.S. Cl. ........................ 568/811; 502/159; 502/163
(58) Field of Search .......................... 568/811; 502/159, 502/163

(56) References Cited

U.S. PATENT DOCUMENTS

| | | | |
|---|---|---|---|
| 4,413,151 A | * 11/1983 | Michaelson et al. | ........ 568/860 |
| 4,496,778 A | * 1/1985 | Myers et al. | ................ 568/860 |
| 5,227,543 A | 7/1993 | Sharpless et al. | |
| 5,260,461 A | 11/1993 | Hartung et al. | |
| 6,197,994 B1 | * 3/2001 | Song et al. | .................... 560/60 |
| 6,297,186 B1 | 10/2001 | Kobayashi | |
| 6,552,234 B1 | * 4/2003 | Choudary et al. | .......... 568/811 |
| 6,646,168 B2 | * 11/2003 | Choudary et al. | .......... 568/811 |

FOREIGN PATENT DOCUMENTS

| | | |
|---|---|---|
| DE | 3920917 | 1/1991 |
| DE | 4210733 | 10/1993 |
| WO | WO 93/17150 | 9/1993 |
| WO | WO 02066158 A | 8/2002 |

OTHER PUBLICATIONS

Choudary et al, "Catalytic Assymetric Dihydroxilation of Olefins With New Catalysts: The First Example of Heterogenization of OsO4(2–) by Ion Exchange Technique", J.A. Chem. Soc., vol. 123, No. 37, 2001, pp. 9220–9221+supporting information, XP 002222261.

Cainelli et al, "Catalytic Hydroxylation of Olefins by Polymer–Bound Osmium Tetroxide", Synthesis, Georg Thieme Verlag, Stuttgart, De, No. 1, 1989, pp. 45–47.

* cited by examiner

Primary Examiner—Michael L. Shippen
(74) Attorney, Agent, or Firm—Nixon & Vanderhye P.C.

(57) ABSTRACT

The present invention provides a supported osmate useful as a reusable catalyst in the preparation of vicinal diols. The present invention also relates to a process for the preparation of supported osmates of the formula $(S-NR_3)_2OsO_4 \cdot nH_2O$ wherein S is a support, R is an alkyl group, n is the number of water molecules and use thereof in the preparation of vicinal diols by asymmetric dihydroxylation (AD) of olefins in presence of cinchona alkaloid compounds.

8 Claims, No Drawings

SUPPORTED OSMATES, PROCESS FOR PREPARATION THEREOF, AND A PROCESS FOR THE PREPARATION OF CHIRAL VICINAL DIOLS USING SUPPORTED OSMATE CATALYST

RELATED APPLICATIONS

This is a division of our earlier application 10/096,071 filed Mar. 13 2002, now U.S. Pat No. 6,646,168 which is a continuation in part of application Ser. No. 09/983,231 filed Oct. 23, 2001 (now U.S. Pat. No. 6,552,234 B1). This application is also related to our prior co-pending application Ser. No. 10/366,611 filed Feb. 14, 2003 as a division of application Ser. No. 09/983,231.

FIELD OF THE INVENTION

The present invention relates to a supported osmate useful as a reusable catalyst in the preparation of vicinal diols. The present invention also relates to a process for the preparation of supported osmates of the formula (S—$NR_3$)$_2$$OsO_4$.$nH_2O$ wherein S is a support, R is an alkyl group, n is the number of water molecules and use thereof in the preparation of vicinal diols by asymmetric dihydroxylation (AD) of olefins in presence of cinchona alkaloid compounds.

BACKGROUND OF THE INVENTION

Asymmetric dihydroxylation of olefins in the presence of cinchona alkaloid results in products that are important intermediates in the preparation of various drugs and chemicals. For example, the products of cinnamic acid esters are intermediates for taxol side chain, an anticancer drug, diltiazem, calcium antagonist and chloramphenicol, an antibiotic. Proranolol, a β blocker can also be derived from diols obtained through this method.

There are serious disadvantages in performing the catalytic AD reaction with homogeneous system in the manufacture of vicinal diols due to presence of toxic remnants of osmium in products and high cost of osmium tetraoxide or potassium osmate dihydrate. By employing the heterogeneous catalytic system, the cost naturally comes down due to easy recovery of the catalyst and very insignificant loss of osmium tetraoxide, when compared with homogeneous system. The products thus obtained using heterogeneous catalyst system are benign in the sense that the presence of osmium in minor impurities in the dihydroxylated products is also precluded.

U.S. Pat. Nos. 4,871,855 and 5,260,421 disclose processes for asymmetric dihydroxylation of olefins using osmium tetraoxide and cinchona alkaloids using homogenous catalyst systems. These processes involve cumbersome recovery of the osmium catalyst from the reaction mixture, generation of toxic waste and the potential presence of toxic osmium in the product.

U.S. Pat. Nos. 5,516,929 and 5,260,461 disclose asymmetric dihydroxylation of olefins using osmium tetraoxide and polymer bound cinchona alkaloids in a heterogeneous system. The quantitative recovery of the toxic osmium catalyst, lower enantioselectivity and reduction in activity and enantioselectivity in each recycle experiments are some of the disadvantages associated with this process.

U.S. Pat. No. 5,968,867 discloses asymmetric dihydroxylation of olefins using osmium tetraoxide and silica gel supported bis-cinchona alkaloid derivatives in a heterogeneous system. Quantitative recovery of toxic osmium catalyst is difficult and a reduction in activity and enantioselectivity of the catalyst is observed in each and every recycle experiment.

European Patent 940,170 A2 describes the catalytic asymmetric dihydroxylation of alkenes using a polymer supported osmium catalyst. The drawbacks of this process are that higher amounts of catalyst are required (5 mol %), the reaction time is very long and expensive polymers are used as supports.

OBJECTS OF THE INVENTION

The main object of the invention is to provide a heterogeneous recyclable supported osmate of the general formula (S—$NR_3$)$_2$$OsO_4$.$nH_2O$ wherein S is a support, R is an alkyl group, n is the number of water molecules and use thereof in the preparation of vicinal diols by asymmetric dihydroxylation (AD) of olefins in presence of cinchona alkaloid compounds.

It is another object of the invention to provide a process for the preparation of a novel heterogeneous recyclable supported osmate of the general formula (S—$NR_3$)$_2$$OsO_4$.$nH_2O$ wherein S is a support, R is an alkyl group, n is the number of water molecules and use thereof in the preparation of vicinal diols.

It is another object of the invention to provide a environmentally friendly process for the asymmetric dihydroxylation of olefins to obtain vicinal diols using a novel heterogeneous supported osmate of the invention.

It is a further object of the invention to provide a process for the preparation of vicinal diols with good enantioselectivity, activity and yield by the asymmetric dihydroxylation of olefins using a novel osmate catalyst of the invention.

It is yet another object of the invention to provide a process for the preparation of vicinal diols by the asymmetric dihydroxylation of olefins in the presence of cinchona alkaloids and derivatives thereof, which process is simple, economical and results in a product with no traces of toxic osmium therein.

It is a further object of the invention to provide a process for the preparation of vicinal diols by the asymmetric dihydroxylation of olefins in the presence of cinchona alkaloids and derivatives thereof wherein the catalyst is capable of recycle several times without substantial loss of activity or in yield of product.

SUMMARY OF THE INVENTION

These and other objects of the invention are achieved by using the novel supported heterogeneous osmate catalyst of the general formula S—$NR_3$)$_2$$OsO_4$.$nH_2O$ wherein S is a support, R is an alkyl group, n is the number of water molecules for the asymmetric dihydroxylation of olefins in the presence of cinchona alkaloids to obtain vicinal diols with good yield and selectivity.

The novelty of the invention lies in the supported osmate catalyst and in preparation of vicinal diols in presence of cinchona alkaloids or derivatives employing oxidants.

Accordingly, the present invention provides a supported osmate of the general formula S—$NR_3$)$_2$$OsO_4$.$nH_2O$ wherein S is a support, R is an alkyl group, n is the number of water molecules.

In one embodiment of the invention, the support is selected from resin and silica.

In another embodiment of the invention, R is selected from methyl, ethyl, propyl, butyl and like alkyl groups.

In a further embodiment of the invention, the osmium content in the catalyst is in the range of 1 to 30%.

In a further embodiment of the invention, the support S as synthesized has charge balancing anions selected from chloride, bromide, iodide, fluoride, hydroxide and acetate.

The invention also relates to a process for the preparation of a novel heterogeneous supported osmate catalyst of the formula S—NR$_3$)$_2$OsO$_4$.nH$_2$O wherein S is a support, R is an alkyl group, n is the number of water molecules, said process comprising reacting potassium osmate with a quaternary ammonium species in water.

In one embodiment of the invention, the potassium osmate is of the formula K$_2$OsO$_4$2H$_2$O.

In another embodiment of the invention, the quaternary ammonium species is of the formula S—NR$_3$X wherein S is a support, R is alkyl and X is selected from Cl, Br, I, F, —OH and OAc.

In a further embodiment of the invention, the reaction is carried out at a temperature in the range of 25 to 100° C. for a period in the range of 5-24 hours.

In one embodiment of the invention, the osmium content in the catalyst is in the range of 1 to 30%.

In another embodiment of the invention, the support S is selected from resin and silica.

In a further embodiment of the invention, the support S as synthesized has charge balancing anions selected from chloride, bromide, iodide, fluoride, hydroxide and acetate.

In another embodiment of the invention, R is selected from methyl, ethyl, propyl, butyl and like alkyl groups.

The present invention also provides a process for the preparation of vicinal diols comprising asymmetrically dihydroxylating the corresponding olefin in the presence of a cinchona alkaloid using an oxidant in a solvent selected from the group consisting of water, acetone, acetonitrile, t-butanol and any mixture thereof, at a temperature in the range of –70 to 100° C. for a period in the range of 0.5 to 24 hours, and in the presence of a catalytic amount of a heterogeneous supported osmate catalyst of the general formula S—NR$_3$)$_2$OsO$_4$.nH$_2$O wherein S is a support, R is an alkyl group, n is the number of water molecules, and recovering the pure vicinal diol.

In one embodiment of the invention, the osmium content in the catalyst is in the range of 1 to 30%.

In another embodiment of the invention, the support S is selected from resin and silica.

In a further embodiment of the invention, the support S used has charge balancing anions selected from chloride, bromide, iodide, fluoride, hydroxide and acetate.

In another embodiment of the invention, R is selected from methyl, ethyl, propyl, butyl and like alkyl groups.

In yet another embodiment of the invention, the amount of supported osmate used in the reaction is 0.01 to 10 mol % of osmium content with respect to the substrate.

In yet another embodiment of the invention the solvent used comprises a solvent system selected from the group consisting of water:acetone, water:acetonitrile and water:t-butanol, the ratio of water to acetone, acetonitrile and t-butanol being in the range of 1:1 to 1:3, and water:acetone:acetonitrile in a ratio of 1:1:1.

In another embodiment of the invention, the catalyst is recovered from the reaction system and recycled to the reaction system as many times as desired.

In a further embodiment of the invention, the oxidant used is selected from the group consisting of N-methylmorpholine N-oxide (NMO), trimethylamine N-oxide, hydrogen peroxide, t-butyl hydrogen peroxide, potassium ferricyanide, sodium periodate and molecular oxygen.

In yet another embodiment of the invention, the cinchona alkaloid and derivatives thereof comprise a monomeric and polymeric chiral ligand.

In a further embodiment of the invention, the chiral ligand is selected from the group consisting of (DHQD)$_2$PHAL, (DHQD)$_2$PYR, (DHQD)$_2$AQN, DHQD-OAc, DHQD-CLB, DHQD-PHN, DHQD-MEQ, DHQD-IND and pseudoenantiomeric forms thereof.

DETAILED DESCRIPTION OF THE INVENTION

The novelty of the invention lies in the supported osmate catalyst and in preparation of vicinal diols in the presence of cinchona alkaloids or derivatives employing oxidants.

The novel supported osmate is of the general formula (S—NR$_3$)$_2$OsO$_4$.nH$_2$O wherein S is a support, R is an alkyl group, n is the number of water molecules. The support is preferably selected from resin or silica R is preferably selected from methyl, ethyl, propyl, butyl and like alkyl groups. The osmium content in the catalyst is generally in the range of 1 to 30%. The support S as synthesized may contain charge balancing anions selected from chloride, bromide, iodide, fluoride, hydroxide and acetate.

The heterogeneous osmate catalyst of the general formula (S—NR$_3$)$_2$OsO$_4$.nH$_2$O wherein S is a support, R is an alkyl group, n is the number of water molecules is prepared by reacting potassium osmate with supported quaternary ammonium species in water as a solvent at a temperature in the range of 25 to 100° C. for a period in the range of 5-24 hours to obtain the desired catalyst.

The process for preparation of vicinal diols comprises asymmetrically dihydroxylating the corresponding olefin in the presence of a cinchona alkaloid compound using an oxidant in a solvent selected from the group consisting of water, acetone, acetonitrile, t-butanol and any mixture thereof at a temperature in the range of –70 to 100° C. for a period in the range of 0.5 to 24 hours, and in the presence of a catalytic amount of a heterogeneous supported osmate catalyst of the general formula (S—NR$_3$)$_2$OsO$_4$.nH$_2$O wherein S is a support, R is an alkyl group, n is the number of water molecules, and recovering the pure vicinal diol by any conventional method. The amount of supported osmate used in the reaction is 0.01 to 10 mol % of osmium content with respect to the substrate.

The catalyst can be recovered from the reaction system by any conventional process and recycled to the reaction system several times without any substantial loss of activity or of yield of the product. The oxidant used is selected from N-methylmorpholine N-oxide (NMO), trimethylamine N-oxide, hydrogen peroxide, t-butyl hydrogen peroxide, potassium ferricyanide, sodium periodate and molecular oxygen. The cinchona alkaloid and derivatives thereof comprise a monomeric and polymeric chiral ligand such as for example (DHQD)$_2$PHAL, (DHQD)$_2$PYR, (DHQD)$_2$AQN, DHQD-OAc, DHQD-CLB, DHQD-PHN, DHQD-MEQ, DHQD-IND and pseudoenantiomeric forms thereof.

Scientific Explanation

In the present invention, novel supported osmates were prepared for the first time using the anion exchange method from the supported quaternary ammonium species. The osmate anions present on the support are responsible for the dihydroxylation activity of the reaction. The activity of the supported osmate is similar or higher than the homogeneous counterparts. Without wishing to be bound by any theory, it is believed that the higher activity is ascribed to the support effect. The large positive potential of $OsO_4^{2-}$ support surface induces polarisation of N→O bond and facilitates oxygen transfer.

Higher yields and enantioselectivities are obtained with supported osmate catalysts used in the asymmetric dihydroxylation of olefins in aqueous organic solvents. Since the dihydroxylated products are important intermediates for the preparation of drugs and pharmaceuticals, this invention is timely and appropriate. Therefore, supported osmate is a better option for the synthesis of vicinol diols. The supported osmate catalysts prepared from various supports offered good yields and enantioselectivies in presence of cinchona alkaloids. Thus this invention offers the best techno-economic route for the synthesis of vicinol diols, intermediates for the preparation of drugs and pharmaceuticals.

Supported osmates are prepared as exemplified and used in catalytic amounts for preparing vicinol diols by asymmetric dihydroxylation of olefins employing oxidants in presence of cinchona alkaloid compounds in a heterogeneous manner as described.

The following examples are given by way of illustration of the present invention and therefore should not be construed to limit the scope of the invention.

Preparation of Catalysts

EXAMPLE 1

Resin-$OsO_4$: Resin was obtained by quaternization of triethylamine (2.1 mL, 21 mmol) with 1 g of chloromethylated styrene-divinylbenzene copolymer (Merrifield resin, capacity-2.1 mequiv/g) in chloroform (20 mL) under reflux for 24 h. 1 g of quaternary ammonium resin was suspended in 100 mL of 0.8 mmol aqueous potassium osmate solution and stirred at 25° C. for 12 h under nitrogen atmosphere. The solid catalyst was filtered, washed thoroughly with 300 mL of water and vacuum dried to obtain Resin-$OsO_4$ (0.641 mmol of Os per g).

EXAMPLE 2

$SiO_2$—$OsO_4$: Modified silica was obtained by quaternisation of triethylamine (0.7 mL, 7 mmol) with bromopropylsilica (capacity 0.7 mequiv/g) in chloroform (20 mL) under reflux for 24 h. 1 g of quaternary ammonium silica was suspended in 100 mL of 0.33 mmol aqueous potassium osmate solution and stirred at 25° C. for 12 h under nitrogen atmosphere. The solid catalyst was filtered, washed thoroughly with 300 mL of water and vacuum dried to obtain $SiO_2$—$OsO_4$ (0.317 mmol of Os per g).

Asymmetric Dihydroxylation of Olefins

The asymmetric dihydroxylation reaction of olefins was performed using the following method in order to evaluate supported osmates of the present invention.

Supported osmate (0.01 eq. wt. of osmium content), bis-cinchona alkaloid $(DHQD)_2PHAL$ (0.01 Eq. Wt.) and N-methylmorpholine-N-oxide (1.5 Eq. Wt.) were stirred in the mixed solvent of water/acetone/acetonitrile (in the volume ratio of 1:1:1). To this mixture was added an olefin (1.0 Eq. Wt) slowly for a period of 12 h. After the reaction, the supported osmate catalyst was filtered off and washed with ethyl acetate. The combined filtrates were concentrated under reduced pressure. The chiral ligand was recovered from the aqueous layer after acidification (1N HCl). The concentrated organic layer was purified to afford the corresponding cis-diol by using conventional processes. The yield and the optical purity of the product were determined.

Catalytic Asymmetric Dihydroxylation of Olefins Using N-Methylmorpholine-N-Oxide as a Co-Oxidant

EXAMPLE 3

Catalytic Asymmetric Dihydroxylation Reaction of Trans-Stilbene by Using Resin-$OsO_4$:

Resin-$OsO_4$ (0.01 eq wt), Hydroquinidine 1,4-phthalazinediyl diether $(DHQD)_2PHAL$ (0.01 eq. wt.) and N-methylmorpholine-N-oxide (1.5 eq. wt.) were stirred in mixed solvent of water/acetone/acetonitrile (volume ratio of 1:1:1). To this mixture trans-stilbene (1.0 eq. wt) was added and stirred at room temperature for 6 hours. After the reaction, supported osmate catalyst was filtered off and washed with methanol. Combined filtrates were concentrated under reduced pressure. Chiral ligand was recovered from aqueous layer after acidification (1N HCl). Pure product was obtained by removing solvent at reduced pressure followed by column chromatography.

(R,R)-(+)-1,2-diphenyl-1,2-ethandiol of more than 99.0% of enantiomeric excess was obtained (yield 96%)

$[\alpha]_D$+92.44 (c 1.0, EtOH): e.e.=99.4%

Catalyst Reusability Experiments

EXAMPLE 4

Catalytic asymmetric dihydroxylation reaction of trans-stilbene by using Resin-$OsO_4$ which had been used in Example 3 without further addition of osmate catalyst.

The reaction was performed using identical process as in Example 3. (R,R)-(+)-1,2-diphenyl-1,2-ethandiol of more than 99.0% of enantiomeric excess was obtained (yield 95%) $[\alpha]_D$+92.90 (c 1.0, EtOH): e.e.=99.9%

EXAMPLE 5

Catalytic asymmetric dihydroxylation reaction of trans stilbene by using Resin-$OsO_4$ which had been used in Example 4 without further addition of supported osmate catalyst.

The reaction was performed by using an identical process as in Example 3. (R,R)-(+)-1,2-diphenyl-1,2-ethandiol of more than 99.0% of enantiomeric excess was obtained (yield 97%)

$[\alpha]_D$+92.16 (c 1.0, EtOH): e.e.=99.1%

EXAMPLE 6

Catalytic asymmetric dihydroxylation reaction of trans-stilbene by using Resin-$OsO_4$ which had been used in Example 5 without further addition of supported osmate catalyst.

The reaction was performed by using identical process as in Example 3. (R,R)-(+)-1,2-diphenyl-1,2-ethandiol of more than 99.0% of enantiomeric excess was obtained (yield 94%)

$[\alpha]_D$+92.25 (c 1.0, EtOH): e.e.=99.2%

EXAMPLE 7

Catalytic asymmetric dihydroxylation reaction of trans-stilbene by using Resin-OsO$_4$ which had been used in Example 6 without further addition of Supported osmate catalyst.

The reaction was performed by using an identical process as in Example 3. (R,R)-(+)-1,2-diphenyl-1,2-ethandiol of more than 99.0% of enantiomeric excess was obtained (yield 96%)

$[\alpha]_D$+92.81 (c 1.0, EtOH): e.e.=99.8%

EXAMPLE 8

Catalytic asymmetric dihydroxylation reaction of trans-stilbene by using Resin-OsO$_4$ which had been used in Example 7 without further addition of supported osmate catalyst.

The reaction was performed by using an identical process as in Example 3. (R,R)-(+)-1,2-diphenyl-1,2-ethandiol of more than 99.0% of enantiomeric excess was obtained (yield 98%)

$[\alpha]_D$+92.25 (c 1.0, EtOH): e.e.=99.2%

EXAMPLE 9

Catalytic asymmetric dihydroxylation reaction of trans-stilbene by SiO$_2$-OsO$_4$ The reaction was performed by using an identical process as in Example 3. (R,R)-(+)-1,2-diphenyl-1,2-ethandiol of more than 99.0% of enantiomeric excess was obtained (yield 97%)

$[\alpha]_D$+92.34 (c 1.0, EtOH): e.e.=99.3%

EXAMPLE 10

Catalytic asymmetric dihydroxylation reaction of styrene by using Resin-OsO$_4$

The reaction was performed by using an identical process as in Example 3 except slow addition of olefin with a reaction time of 12 hours. (R)-phenyl-1,2-ethanediol of more than 95.0% of enantiomeric excess was obtained (yield 94%) $[\alpha]_D$ −34.29 (c 1.32, EtOH): e.e.=95.7%

EXAMPLE 11

Catalytic asymmetric dihydroxylation reaction of trans-beta-methyl styrene by using Resin-OsO$_4$ The reaction was performed by using an identical process as in Example 3 except slow addition of olefin with a reaction time of 12 hours. (R,R)-1-phenyl-1,2-propanediol of more than 98.0% of enantiomeric excess was obtained (yield 97%)

$[\alpha]_D$ −30.50 (c 1.32, EtOH): e.e.=98.1%

EXAMPLE 12

Catalytic asymmetric dihydroxylation reaction of methyl trans-cinnamate by using Resin-OsO$_4$.

The reaction was performed by using an identical process as in Example 3 except slow addition of olefin with a reaction time of 12 hours. (2S,3R)-2,3-dihydroxy-3-phenylpropionate of more than 99% of enantiomeric excess was obtained (yield 96%)

$[\alpha]_D$ −10.6 (c 1.0, CHCl$_3$): e.e.=99%

EXAMPLE 13

Catalytic asymmetric dihydroxylation reaction of allyl 1-naphthyl ether by using Resin-OsO$_4$ The reaction was performed by using an identical process as in Example 3 except slow addition of olefin with a reaction time of 12 hours. 2,3-dihydroxypropyl-1-naphthyl ether of more than 77.0% of enantiomeric excess was obtained (yield 94%)

$[\alpha]_D$ +5.18 (c 1.0, CH$_3$OH): e.e.=77.4%

EXAMPLE 14

Catalytic dihydroxylation reaction of trans-stilbene by using Resin-OsO$_4$:

Resin-OsO$_4$ (0.01 Eq. Wt.), N-methylmorpholine-N-oxide (1.5 Eq. Wt.) and trans-stilbene (1.0 Eq. Wt) in the mixed solvent of water/acetone/acetonitrile (in the volume ratio of 1:1:1) were stirred at room temperature for 6 hours. After completion of the reaction, the catalyst was filtered off and washed with ethyl acetate. Combined filtrates were concentrated under reduced pressure. The pure product, 1,2-diphenyl-1,2-ethandiol was obtained by removing the solvent reduced pressure followed by column chromatography. (yield 93%).

The experimental results in the Examples 3 to 14 are tabulated in Tables 1 and 2.

TABLE 1

Reuse of Resin-OsO$_4$ for asymmetric dihydroxylation reaction of trans-stilbene

| Ex.No | run | Yield | ee |
|---|---|---|---|
| 3 | 1 | 96 | 99.4 |
| 4 | 2 | 95 | 99.9 |
| 5 | 3 | 97 | 99.1 |
| 6 | 4 | 94 | 99.2 |
| 7 | 5 | 96 | 99.8 |
| 8 | 6 | 98 | 99.2 |

TABLE 2

Catalytic asymmetric dihydroxylation reaction of olefins by using Resin-OsO$_4$

| Ex.No | Catalyst[a] | Ligand | Olefin | Time | Yield[b] | ee[c] | Config.[d] |
|---|---|---|---|---|---|---|---|
| 9 | SiO$_2$—OsO$_4$ | (DHQD)$_2$PHAL | Trans-stilbene | 6 | 97 | 99.3 | RR |
| 10 | Resin-OsO$_4$ | (DHQD)$_2$PHAL | Styrene | 12 | 94 | 95.7 | R |
| 11 | Resin-OsO$_4$ | (DHQD)$_2$PHAL | E-Methylstyrene | 12 | 97 | 98.1 | RR |
| 12 | Resin-OsO$_4$ | (DHQD)$_2$PHAL | E-Methylcinnamate | 12 | 96 | 99.0 | 2S, 3R |

TABLE 2-continued

Catalytic asymmetric dihydroxylation reaction of olefins by using Resin-OsO$_4$

| Ex.No | Catalyst[a] | Ligand | Olefin | Time | Yield[b] | ee[c] | Config.[d] |
|---|---|---|---|---|---|---|---|
| 13 | Resin-OsO$_4$ | (DHQD)$_2$PHAL | Allyl 1-naphrhyl ether | 12 | 94 | 77.4 | S |
| 14 | Resin-OsO$_4$ | — | Trans-stilbene | 6 | 93 | — | — |

[a]Equivalent weight ratio of the reactants = olefin: osmium: cinchona alkaloid = 1:0.01:0.01, reaction temperature 25° C.
[b]Yield percent after the separation by using column chromatography.
[c]% e.e.(e.e. means enantiomeic excess) was determined by HPLC analysis using chiral columns
[d]absolute configuration was compared with the [α]$_D$ values in the literature.

Solvent effects:

EXAMPLE 15

Catalytic asymmetric dihydroxylation reaction of trans-stilbene by Resin-OsO$_4$:

The reaction was performed by an identical process as in Example 3 except the solvent is water/acetone (in the volume ratio of 1:3). (R,R)-(+)-1,2-diphenyl-1,2-ethandiol of more than 99.0% of enantiomeric excess was obtained (yield 95%)

[α]$_D$ +91.90 (c 1.0, EtOH): e.e.=99.0%

EXAMPLE 16

Catalytic asymmetric dihydroxylation reaction of trans-stilbene by Resin-OsO$_4$:

The reaction was performed by an identical process as in Example 3 except the solvent is water/acetonitrile (in the volume ratio of 1:3). (R,R)-(+)-1,2-diphenyl-1,2-ethandiol of more than 99.0% of enantiomeric excess was obtained (yield 93%)

[α]$_D$ +91.1 (C 1.0, EtOH): e.e.=99.0%

EXAMPLE 17

Catalytic asymmetric dihydroxylation reaction of trans-stilbene by Resin-OsO$_4$:

The reaction was performed by an identical process as in Example 3 except the solvent is water/t-butanol (volume ratio of 1:3) and the reaction time is 24 h (R,R)-(+)-1,2-diphenyl-1,2-ethandiol of more than 99.0% of enantiomeric excess was obtained (yield 91%)

[α]$_D$ +91.6 (c 1.0, EtOH): e.e.=99.0%

EXAMPLE 18

Catalytic asymmetric dihydroxylation reaction of trans-stilbene by Resin-OsO$_4$:

The reaction was performed by an identical process as in Example 3 except the solvent is water/t-butanol (volume ratio of 1:2) and the reaction time is 24 h (R,R)-(+)-1,2-diphenyl-1,2-ethandiol of more than 99.0% of enantiomeric excess was obtained (yield 90%)

[α]$_D$ +92.1 (c 1.0, EtOH): e.e.=99.0%

EXAMPLE 19

Catalytic asymmetric dihydroxylation reaction of trans-stilbene by Resin-OsO$_4$:

The reaction was performed by an identical process as in Example 3 except the solvent is water/t-butanol (volume ratio of 1:1) and the reaction time is 36 h (R,R)-(+)-1,2-diphenyl-1,2-ethandiol of more than 99.0% of enantiomeric excess was obtained (yield 92%)

[α]$_D$ +92.3 (c 1.0, EtOH): e.e.=99.0%

TABLE 3

Solvent effects in catalytic asymmetric dihydroxylation reaction of trans-stilbene by Resin-OsO$_4$

| Ex. No | Catalyst[a] | Ligand | Olefin | Time | Yield[b] | ee[c] | Config.[d] |
|---|---|---|---|---|---|---|---|
| 15 | Resin-OsO$_4$ | (DHQD)$_2$PHAL | Trans-stilbene | 6 | 95 | 99 | RR |
| 16 | Resin-OsO$_4$ | (DHQD)$_2$PHAL | Trans-stilbene | 6 | 93 | 99 | RR |
| 17 | Resin-OsO$_4$ | (DHQD)$_2$PHAL | Trans-stilbene | 24 | 91 | 99 | RR |
| 18 | Resin-OsO$_4$ | (DHQD)$_2$PHAL | Trans-stilbene | 24 | 90 | 99 | RR |
| 19 | Resin-OsO$_4$ | (DHQD)$_2$PHAL | Trans-stilbene | 36 | 92 | 99 | RR |

The main advantages of the present invention are:
1. A novel and ecofriendly process for asymmetric dihydroxylation of olefins is presented.
2. The present process dispenses the use of soluble, toxic osmium tetraoxide or potassium osmate dihydrate instead heterogeneous reusable supported osmates are used.
3. Supported osmates are prepared and used for asymmetric dihydroxylation of olefins as heterogeneous catalysts. The use of heterogeneous supported osmates precludes the presence of osmium in traces with product.
4. The enantioselectivity and the yields are good.
5. The work-up procedure is simple.
6. The catalyst is subjected to many recycles, which displayed consistent activity.
7. The present process is environmentally safe since there is no disposal problem.
8. The process is economical

We claim:
1. A process for the preparation of a novel heterogeneous supported osmate catalyst of the formula (S—NR$_3$)$_2$OsO$_4$.nH$_2$O wherein S is a support, R is an alkyl group, n is the number of water molecules, said process comprising reacting potassium osmate with a quaternary ammonium species in water.

2. A process as claimed in claim 1 wherein the potassium osmate is of the formula $K_2OsO_4 2H_2O$.

3. A process as claimed in claim 1 wherein the quaternary ammonium species is of the formula $S-NR_3X$ wherein S is a support, R is a alkyl, and X is selected from Cl, Br, I, F, —OH and OAc.

4. A process as claimed in claim 1 wherein the reaction is carried out at a temperature in the range of 25 to 100° C. for a period in the range of 5–24 hours.

5. A process as claimed in claim 1 wherein the osmium content in the catalyst is in the range of 1 to 30%.

6. A process as claimed in claim 1 wherein the support S is selected from resin and silica.

7. A process as claimed in claim 1 wherein the support S as synthesized has charge balancing anions selected from chloride, bromide, iodide, fluoride, hydroxide and acetate.

8. A process as claimed in claim 1 wherein is R is alkyl selected from methyl, ethyl, propyl and butyl groups.

* * * * *